US009832411B2

(12) United States Patent
Okura et al.

(10) Patent No.: US 9,832,411 B2
(45) Date of Patent: Nov. 28, 2017

(54) TRANSMISSION SYSTEM AND PROCESSING DEVICE

(71) Applicant: OLYMPUS CORPORATION, Tokyo (JP)

(72) Inventors: Sachiko Okura, Tokyo (JP); Takehiko Ito, Saitama (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/209,153

(22) Filed: Jul. 13, 2016

(65) Prior Publication Data

US 2016/0323531 A1    Nov. 3, 2016

Related U.S. Application Data

(63) Continuation of application No. PCT/JP2015/076542, filed on Sep. 17, 2015.

(30) Foreign Application Priority Data

Sep. 26, 2014  (JP) .................................. 2014-196951

(51) Int. Cl.
*H04N 5/38* (2006.01)
*A61B 1/04* (2006.01)
(Continued)

(52) U.S. Cl.
CPC ........... *H04N 5/38* (2013.01); *A61B 1/00004* (2013.01); *A61B 1/00006* (2013.01);
(Continued)

(58) Field of Classification Search
CPC ........ H04N 5/38; H04N 7/185; H04N 5/2256; H04N 5/04; H04N 2005/2255;
(Continued)

(56) References Cited

U.S. PATENT DOCUMENTS 5,442,452 A * 8/1995 Ryu .......................... H04N 5/45
                                                       348/462
8,970,686 B2    3/2015 Kobayashi et al.
(Continued)

FOREIGN PATENT DOCUMENTS

JP    2000-244827 A    9/2000
JP    2001-268529 A    9/2001
(Continued)

OTHER PUBLICATIONS

International Search Report dated Dec. 1, 2015 issued in PCT/JP2015/076542.

*Primary Examiner* — Jay Patel
*Assistant Examiner* — Joseph Suh
(74) *Attorney, Agent, or Firm* — Scully, Scott, Murphy & Presser, P.C.

(57) ABSTRACT

A transmission system includes: a first timing signal generation unit; a second timing signal generation unit; a timing adjustment unit; a transmission processing unit; a first valid data generation unit which receives a first timing signal, receives only data according to valid timing of the first timing signal in a first image signal from a process signal to generate a first valid image signal, and receives only data according to valid timing of the first timing signal in a second image signal and a second timing signal from the process signal to output the received second image signal and the received second timing signal; and a second valid data generation unit which receives the second timing signal from the first valid data generation unit and receives only data according to valid timing of the second timing signal in the second image signal to generate a second valid image signal.

1 Claim, 4 Drawing Sheets

(51) Int. Cl.

| | | |
|---|---|---|
| *A61B 1/00* | (2006.01) | |
| *A61B 1/005* | (2006.01) | |
| *A61B 1/07* | (2006.01) | |
| *H04N 5/04* | (2006.01) | |
| *H04N 5/225* | (2006.01) | |
| *H04N 7/18* | (2006.01) | |
| *G09G 5/00* | (2006.01) | |
| *A61B 1/045* | (2006.01) | |

(52) U.S. Cl.
CPC ...... *A61B 1/00009* (2013.01); *A61B 1/00011* (2013.01); *A61B 1/00045* (2013.01); *A61B 1/0051* (2013.01); *A61B 1/04* (2013.01); *A61B 1/045* (2013.01); *A61B 1/07* (2013.01); *G09G 5/006* (2013.01); *H04N 5/04* (2013.01); *H04N 5/2256* (2013.01); *H04N 7/185* (2013.01); *H04N 2005/2255* (2013.01)

(58) Field of Classification Search
CPC G09G 5/006; G09G 5/00; G09G 5/18; G09G 5/391; A61B 1/0051; A61B 1/00045; A61B 1/00011; A61B 1/00004; A61B 1/07; A61B 1/04
See application file for complete search history.

(56) References Cited

U.S. PATENT DOCUMENTS

| | | | | |
|---|---|---|---|---|
| 2002/0097333 | A1* | 7/2002 | Wechsler | G06Q 30/02 348/373 |
| 2003/0025789 | A1* | 2/2003 | Saito | A61B 1/00041 348/76 |
| 2003/0048383 | A1* | 3/2003 | Casteleyn | H04N 5/44591 348/565 |
| 2004/0168094 | A1* | 8/2004 | Chen | G06F 1/26 713/300 |
| 2006/0031593 | A1* | 2/2006 | Sinclair | G06F 13/42 709/251 |
| 2006/0238826 | A1* | 10/2006 | Itou | H04N 21/6125 358/448 |
| 2007/0195111 | A1* | 8/2007 | Yao | G06F 3/1438 345/634 |
| 2007/0274577 | A1* | 11/2007 | De Font-Reaulx-Rojas | A61B 1/00193 382/128 |
| 2008/0055697 | A1* | 3/2008 | Okazaki | H04N 1/047 359/238 |
| 2009/0109988 | A1* | 4/2009 | Musunuri | G06F 3/14 370/412 |
| 2009/0153675 | A1* | 6/2009 | Owashi | H04N 5/12 348/207.99 |
| 2009/0278984 | A1* | 11/2009 | Suzuki | G09G 5/003 348/554 |
| 2011/0205433 | A1* | 8/2011 | Altmann | H04N 9/475 348/513 |
| 2013/0231185 | A1* | 9/2013 | Steil | G07F 17/3211 463/35 |
| 2014/0028913 | A1* | 1/2014 | Deng | H04N 5/23293 348/500 |
| 2016/0015367 | A1* | 1/2016 | Schneider | A61B 8/0883 600/437 |

FOREIGN PATENT DOCUMENTS

| | | |
|---|---|---|
| JP | 2003-024273 A | 1/2003 |
| JP | 2006-255109 A | 9/2006 |
| JP | 2013-022054 A | 2/2013 |

\* cited by examiner

TRANSMISSION SYSTEM AND PROCESSING DEVICE

CROSS-REFERENCE TO RELATED APPLICATIONS

This application is a continuation of PCT international application Ser. No. PCT/JP2015/076542 filed on Sep. 17, 2015 which designates the United States, incorporated herein by reference, and which claims the benefit of priority from Japanese Patent Applications No. 2014-196951, filed on Sep. 26, 2014, incorporated herein by reference.

BACKGROUND

1. Field of the Disclosure

The present disclosure relates to a transmission system performing transmission of an image signal and a processing device performing a signal process of an image signal.

2. Description of the Related Art

In the related arts, endoscope systems are used for observing organs of a subject such as a patient in medical fields. For example, the endoscope system is configured to include an endoscope having an inserting unit which is provided with an image sensor at a distal end thereof and is inserted into a subject and a processing device which is connected to a proximal end side of the inserting unit through a cable to perform an image process on an in-vivo image according to the imaging signal generated by the image sensor and display the in-vivo image on a display unit or the like.

In recent years, the display units have displayed the in-vivo images at a high image quality. In order to achieve the high image quality, disclosed is a processing device which can perform an image process on an imaging signal output from an image sensor provided to an endoscope to convert the imaging signal to a high definition television (HDTV) image signal (refer to, for example, JP 2003-24273 A). The processing device disclosed in JP 2003-24273 A can also convert the imaging signal to a standard definition television (SDTV) image signal as well as the HDTV image signal and can display in-vivo images on a monitor according to resolution.

SUMMARY

A transmission system according to one aspect of the present disclosure transmits a plurality of image signals having different clock rates, each of which includes valid timing and invalid timing, and includes: a first timing signal generation unit which receives a first image signal having the highest clock rate among the plurality of image signals and generates a first timing signal representing valid timing and invalid timing of the first image signal; a second timing signal generation unit which receives a second image signal other than the first image signal and generates a second timing signal representing valid timing and invalid timing of the second image signal, each valid timing of the second timing signal being synchronized with the valid timing of the first timing signal; a timing adjustment unit which receives the first timing signal and the second image signal and outputs the second image signal based on the first timing signal; a transmission processing unit which receives the first and second timing signals and the first and second image signals and individually outputs the first timing signal and a process signal including the first and second image signals and the second timing signal; a first valid data generation unit which receives the first timing signal from the transmission processing unit, receives only data according to valid timing of the first timing signal in the first image signal from the process signal to generate a first valid image signal, and receives only data according to valid timing of the first timing signal in the second image signal and the second timing signal from the process signal to output the received second image signal and the received second timing signal; and a second valid data generation unit which receives the second timing signal from the first valid data generation unit and receives only data according to valid timing of the second timing signal in the second image signal to generate a second valid image signal.

A processing device according to another aspect of the present disclosure, which is connected to an imaging device including an imaging unit imaging an imaging object to output an imaging signal and applies a predetermined process based on the imaging signal imaged by the imaging device, includes: an image signal generation unit which generates a plurality of image signals having different clock rates; a transmission unit including a first timing signal generation unit which receives a first image signal having the highest clock rate among the plurality of image signals and generates a first timing signal representing valid timing and invalid timing of the first image signal, a second timing signal generation unit which receives a second image signal other than the first image signal and generates a second timing signal representing valid timing and invalid timing of the second image signal, each valid timing of the second timing signal being synchronized with the valid timing of the first timing signal, a timing adjustment unit which receives the first timing signal and the second image signal and outputs the second image signal based on the first timing signal, a transmission processing unit which receives the first and second timing signals and the first and second image signals and individually outputs the first timing signal and a process signal including the first and second image signals and the second timing signal, a first valid data generation unit which receives the first timing signal from the transmission processing unit, receives only data according to valid timing of the first timing signal in the first image signal from the process signal to generate a first valid image signal, and receives only data according to valid timing of the first timing signal in the second image signal and the second timing signal from the process signal to output the received second image signal and the received second timing signal, and a second valid data generation unit which receives the second timing signal from the first valid data generation unit and receives only data according to valid timing of the second timing signal in the second image signal to generate a second valid image signal; and an image processing unit which applies a signal process for display image to the first and second valid image signals output by the transmission unit.

The above and other objects, features, advantages and technical and industrial significance of this disclosure will be better understood by reading the following detailed description of presently preferred embodiments of the disclosure, when considered in connection with the accompanying drawings.

DETAILED DESCRIPTION

Figure 1:
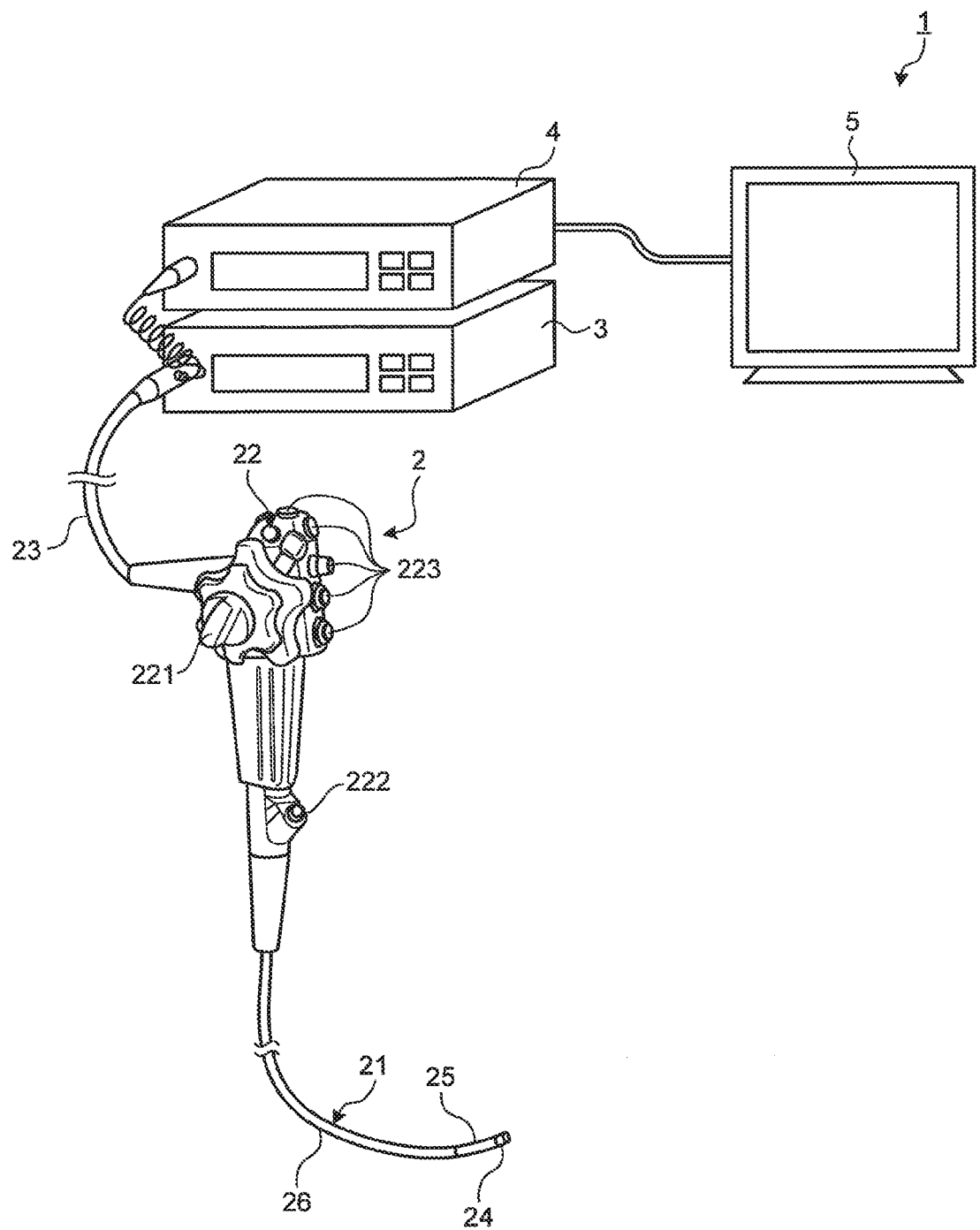
FIG. 1 is a diagram illustrating a schematic configuration of an endoscope system according to an embodiment of the present disclosure.

Hereinafter, an aspect (hereinafter, referred to as an "embodiment") for embodying the present disclosure will be described. In the embodiment, a medical endoscope system capturing an image inside a subject such as a patient and displaying the image as an example of a system including a transmission system and a processing device according to the present disclosure will be described. In addition, the present disclosure is not limited to the embodiment. In addition, in the description of the drawings, the same components are denoted by the same reference numerals.

Figure 2:
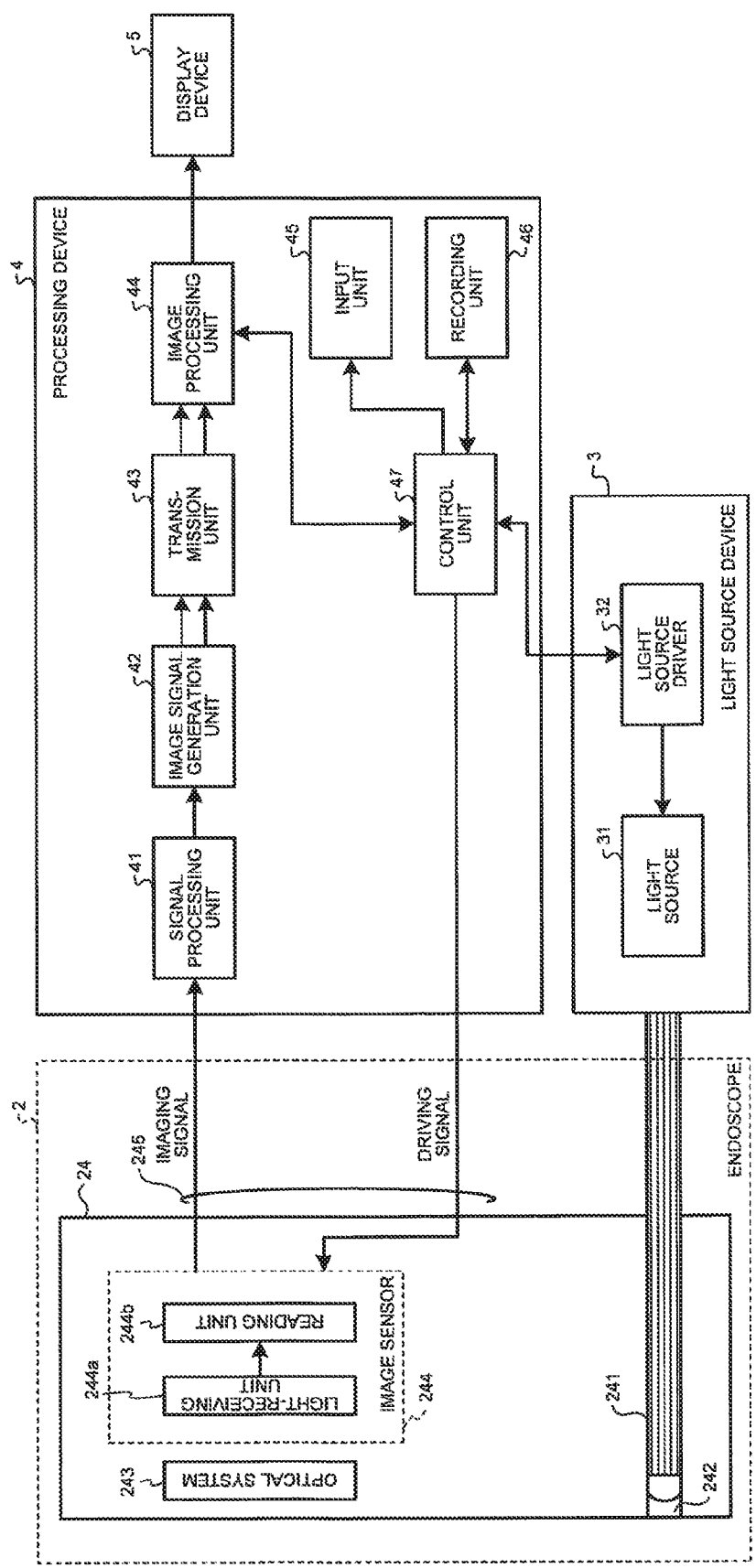
FIG. 2 is a block diagram illustrating a schematic configuration of the endoscope system according to the embodiment of the present disclosure.

FIG. 1 is a diagram illustrating a schematic configuration of an endoscope system according to an embodiment of the present disclosure. FIG. 2 is a block diagram illustrating a schematic configuration of the endoscope system according to the embodiment.

The endoscope system 1 illustrated in FIGS. 1 and 2 is configured to include an endoscope 2 which captures an in-vivo image of a subject by inserting a distal end portion into a body cavity of the subject, a light source device 3 which generates illumination light which is to be emitted from an distal end of the endoscope 2, a processing device 4 which performs a predetermined signal process on an imaging signal captured by the endoscope 2 and controls overall operations of the endoscope system 1, and a display device 5 which displays the in-vivo image generated by the signal process of the processing device 4.

The endoscope 2 is configured to include an inserting unit 21 which has flexibility and is formed in an elongated shape, an operating unit 22 which is connected to a proximal end of the inserting unit 21 and receives input of various operating signals, and a universal cord 23 which is extended from the operating unit 22 in a direction different from an extension direction of the inserting unit 21 and incorporates various cables which are to be connected to the light source device 3 and the processing device 4.

The inserting unit 21 is configured to include a distal end portion 24 which incorporates an image sensor 244 where pixels generating a signal by receiving light and performing photoelectric conversion are arrayed in a two-dimensional shape, a bendable bending portion 25 configured with a plurality of bending pieces, and a flexible tube portion 26 having flexibility and being in an elongated shape which is connected to a proximal end side of the bending portion 25.

The distal end portion 24 is configured to include a light guide 241 which is configured by using a glass fiber or the like to form a light guide path of the light emitted by the light source device 3, an illumination lens 242 which is provided to a distal end of the light guide 241, an optical system 243 for collecting light, and the image sensor 244 which is provided at an imaging position of the optical system 243 to receive the light collected by the optical system 243, perform photoelectric conversion on an electric signal, and apply a predetermined signal process.

The optical system 243 is configured by using one lens or a plurality of lenses and has an optical zoom function of changing an angle of view and a focus function of changing a focus.

The image sensor 244 photoelectrically converts the light from the optical system 243 to generate an electric signal (imaging signal). More specifically, the image sensor 244 is configured to include a light-receiving unit 244a where a plurality of pixels, each of which includes a photodiode storing charges according to a light amount, a condenser converting the charges transferred from the photodiode to a voltage level, and the like, are arrayed in a matrix shape and each pixel photoelectrically converts the light from the optical system 243 to generate an electric signal, and a reading unit 244b which sequentially reads the electric signal generated by the pixels arbitrarily set as a to-be-read object among the plurality of pixels of the light-receiving unit 244a and outputs the electric signal as an imaging signal. The image sensor 244 controls various operations of the distal end portion 24 according to driving signals received from the processing device 4. The image sensor 244 is implemented by using, for example, a charge coupled device (CCD) image sensor or a complementary metal oxide semiconductor (CMOS) image sensor. In the embodiment, the image sensor 244 is described to output an imaging signal according to a high definition television (HDTV) image signal.

The operating unit 22 is configured to include a bending knob 221 bending the bending portion 25 in the up/down direction and the left/right direction, a treatment-tool inserting unit 222 inserting a treatment tool such as biological forceps, electric scalpel, and a biopsy probe into a subject, and a plurality of switches 223 which are operation inputs unit inputting operation instruction signals for peripheral devices such as an air supply means, a water supply means, and a screen display controller in addition to the processing device 4 and the light source device 3. The treatment tool inserted from the treatment-tool inserting unit 222 is exposed to an opening (not illustrated) through a treatment-tool channel (not illustrated) of the distal end portion 24.

The universal cord 23 incorporates at least the light guide 241 and a collective cable 245 formed by bundling one signal line or a plurality of signal lines. The collective cable 245 includes signal lines for transmitting the imaging signals, signal lines for transmitting the driving signals for driving the image sensor 244, and signal lines for transmitting and receiving unique information on the endoscope 2 (image sensor 244).

Next, the configuration of the light source device 3 will be described. The light source device 3 is configured to include a light source 31 and a light source driver 32.

The light source 31 is configured by using an LED light source emitting white light and one lens or a plurality of lenses and emits light (illumination light) by driving the LED light source under the control of the light source driver 32. The illumination light generated by the light source 31 is emitted to the subject from the distal end of the distal end portion 24 through the light guide 241. In addition, the light source 31 may be configured by using a red LED light source, a green LED light source, and a blue LED light source to emit light from any one of the light sources and may emit light having a wavelength range among red light, green light, and blue light as illumination light.

The light source driver 32 supplies a current to the LED light source of the light source 31 to allow the LED light source to emit the illumination light. The light source driver 32 controls a power amount which is to be supplied to the light source 31 (LED light source) and controls driving timing of the light source 31 based on control signals from a control unit 47 of the processing device 4.

Next, a configuration of the processing device 4 will be described. The processing device 4 is configured to include a signal processing unit 41, an image signal generation unit 42, a transmission unit 43 (transmission system), an image processing unit 44, an input unit 45, a recording unit 46, and the control unit 47.

The signal processing unit 41 performs noise removal or A/D conversion on the imaging signal output by the image sensor 244.

The image signal generation unit 42 generates a plurality (two in the embodiment) of image signals having different clock rates based on the imaging signal input from the signal processing unit 41. More specifically, the image signal generation unit 42 generates two image signals (first and second image signals) having valid timing and invalid timing at arbitrary timing. In the embodiment, it is described that a clock rate of the first image signal is higher than that of the second image signal. Namely, the first image signal is described as a first image signal, and the second image signal is described as a second image signal. The image signal generation unit 42 receives, for example, an image signal according to an HDTV image signal (for example, a clock frequency: 74 MHz) to generate the first image signal according to the HDTV image signal and decreases the clock rate of the received image signal to generate the second image signal according to a standard definition television (SDTV) image signal (for example, a clock frequency: 27 MHz).

The transmission unit 43 extracts respective data of valid timing from the first and second image signals received from the image signal generation unit 42 and outputs the first and second valid image signals. In other words, the transmission unit 43 removes data according to invalid timing from the image signal received from the image signal generation unit 42 and performs extraction of the data which are to be displayed on a monitor.

The image processing unit 44 generates an image signal for display which is to be displayed by the display device 5 based on the first and second valid image signals input from the transmission unit 43. The image processing unit 44 performs a predetermined signal process on the image signal in each standard to generate the image signal for display which includes an in-vivo image. Herein, as the signal processes, there are a synchronization process (performed in the case where an imaging signal is acquired by using, for example, a color filter or the like), an optical black subtraction process, a white balance adjustment process, a color matrix calculation process, a gamma correction process, a color reproduction process, an edge enhancement process, a format conversion process, and the like. The image processing unit 44 outputs the generated image signal to the display device 5.

The input unit 45 receives input of various signals such as an operation instruction signal of instructing the operations of the endoscope system 1.

The recording unit 46 is implemented by using a semiconductor memory such as a flash memory or a dynamic random access memory (DRAM). The recording unit 46 records various programs for operating the endoscope system 1 and data including various parameters necessary for the operations of the endoscope system 1. In addition, the recording unit 46 records identification information of the processing device 4. Herein, the identification information includes unique information (ID), production year, specification information, and the like of the processing device 4.

The control unit 47 is configured by using a CPU and the like and performs driving control of the components including the image sensor 244 and the light source device 3 and input/output control of information with respect to each component. The control unit 47 refers to control information data (for example, read timing and the like) for imaging control which are recorded in the recording unit 46 and transmits the control information data to the image sensor 244 through a predetermined signal line included in the collective cable 245.

Next, the display device 5 will be described. The display device 5 receives an in-vivo image corresponding to the image signal generated by the processing device 4 through an image cable and displays the in-vivo image. The display device 5 is configured by using a monitor such as a liquid crystal display or an organic electroluminescence (EL) display device.

Figure 3:
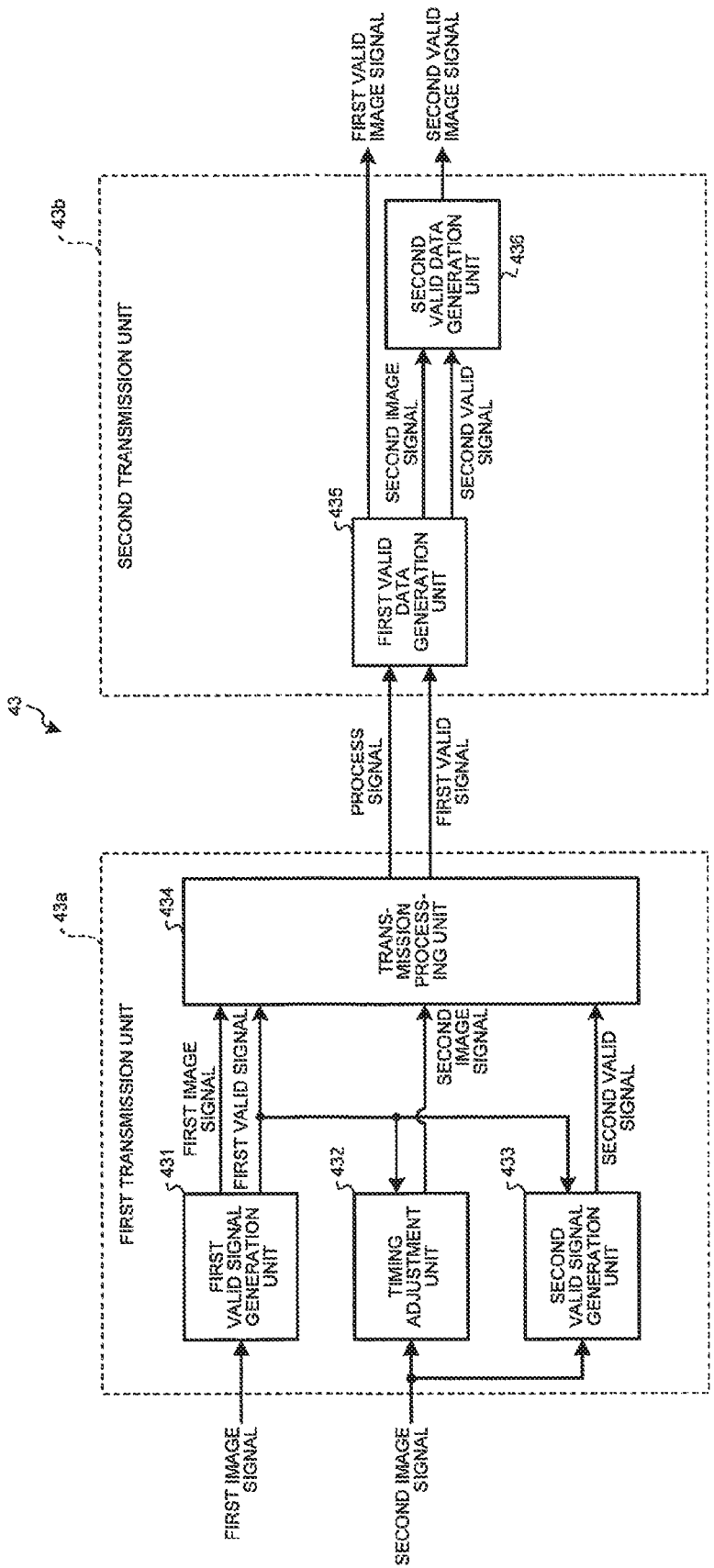
FIG. 3 is a block diagram illustrating a schematic configuration of a transmission unit of the endoscope system according to the embodiment of the present disclosure.

Subsequently, the transmission process by the transmission unit 43 of the endoscope system 1 will be described with reference to FIGS. 3 and 4. FIG. 3 is a block diagram illustrating a schematic configuration of the transmission unit of the endoscope system according to the embodiment. The transmission unit 43 is configured to include a first transmission unit 43a and a second transmission unit 43b. The first transmission unit 43a is configured to include a first valid signal generation unit 431 (first timing signal generation unit), a timing adjustment unit 432, a second valid signal generation unit 433 (second timing signal generation unit), and a transmission processing unit 434. The second transmission unit 43b is configured to include a first valid data generation unit 435 (first valid data generation unit) and a second valid data generation unit 436 (second valid data generation unit).

The first valid signal generation unit 431 generates a first valid signal (first timing signal) which becomes "High" at valid timing and "Low" at invalid timing based on the first image signal received from the image signal generation unit 42. The first valid signal becomes "High" (valid timing) at a timing corresponding to a start timing of frames constituting one sheet of image. The first valid signal generation unit 431 outputs the first image signal after the generation of the first valid signal to the transmission processing unit 434 and outputs the generated first valid signal to the timing adjustment unit 432, the second valid signal generation unit 433, and the transmission processing unit 434.

The timing adjustment unit 432 synchronizes the valid timing of the second image signal with the first valid signal generated by the first valid signal generation unit 431 to output the second image signal to the transmission processing unit 434. The timing adjustment unit 432 first processes and outputs first-coming-in data and later processes and outputs later-coming-in data. The timing adjustment unit 432 is implemented by using a memory, for example, a first-in first-out (FIFO) memory, or the like.

The second valid signal generation unit 433 generates a second valid signal (second timing signal) which becomes "High" at valid timing and "Low" at invalid timing based on the second image signal received from the image signal generation unit 42. Similarly to the first valid signal, the second valid signal also becomes "High" (valid timing) at a timing corresponding to a start timing of frames. In addition, the second valid signal generation unit 433 synchronizes the generated second valid signal with the first valid signal and outputs the second valid signal to the transmission processing unit 434.

Figure 4:
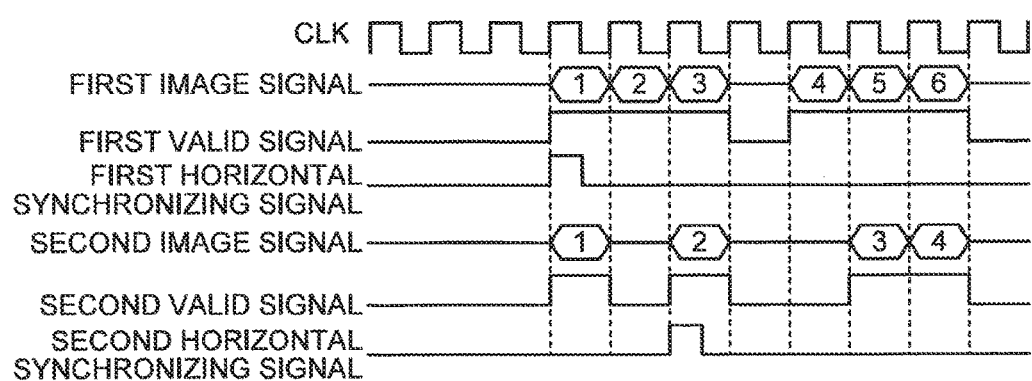
FIG. 4 is a timing chart illustrating a transmission mode of electric signals in the transmission unit of the endoscope system according to the embodiment of the present disclosure.

FIG. 4 is a timing chart illustrating a transmission mode of electric signals in the transmission unit of the endoscope system according to the embodiment of the present disclosure. In addition, in FIG. 4, numbers attached to the image signals denote frame numbers (frame 1, frame 2, frame 3, frame 4, . . . ) given to the frames. In addition, in FIG. 4, CLK denotes a clock signal. The signals output from the first valid signal generation unit 431, the timing adjustment unit 432, and the second valid signal generation unit 433 are output to the transmission processing unit 434 in the state that the valid timing of the second image signal and the valid timing of the second valid signal are included in the valid timing ("High" state) of the first valid signal, as illustrated in FIG. 4.

With respect to the received first and second image signals and the received first and second valid signals, the transmission processing unit 434 outputs the valid signal (in the embodiment, the first valid signal) generated based on the image signal (in the embodiment, the first image signal) having the highest clock rate to the first valid data generation unit 435 of the second transmission unit 43b and outputs the first and second image signals and the second valid signal as process signals to the first valid data generation unit 435. In other words, the transmission processing unit 434 outputs the first valid signal individually to the first valid data generation unit 435 and outputs the process signals including the first and second image signals and the second valid signal to the first valid data generation unit 435.

The first valid data generation unit 435 receives only the data of the valid timing (first valid signal is in the "High" state) in the process signals (the first and second image signals and the second valid signal) output by the transmission processing unit 434 based on the received first valid signal. Namely, the first image signal is recovered to a signal (hereinafter, referred to as a first valid image signal) having a waveform where the data of the invalid timing do not exist by a determination process of the first valid data generation unit 435. At this time, in addition to the first valid image signal, the synchronizing signal (for example, the first horizontal synchronizing signal illustrated in FIG. 4) is also recovered. The first valid data generation unit 435 outputs the received first valid image signal (including the synchronizing signal) to the image processing unit 44.

On the other hand, the first valid data generation unit 435 receives the data of the valid timing (first valid signal is in the "High" state) in the second image signal. Namely, the second image signal becomes a signal (signal including a portion of the invalid data of the second valid signal) having a waveform where the data of the valid timing of the first valid signal exist by a determination process of the first valid data generation unit 435. The first valid data generation unit 435 outputs the received second image signal to the second valid data generation unit 436. In addition, like the above-described receiving process, the first valid data generation unit 435 receives the data of the valid timing (first valid signal is in the "High" state) in the second valid signal.

The second valid data generation unit 436 receives only the data of the valid timing (second valid signal is in the "High" state) in the second image signal output by the first valid data generation unit 435 based on the second valid signal received from the first valid data generation unit 435. Namely, the second image signal output by the first valid data generation unit 435 is recovered to a signal (hereinafter, referred to as a second valid image signal) having a waveform where the data of the invalid timing do not exist by a determination process of the second valid data generation unit 436. At this time, in addition to the second valid image signal, the synchronizing signal (for example, the second horizontal synchronizing signal illustrated in FIG. 4) is also recovered. The second valid data generation unit 436 outputs the received second valid image signal to the image processing unit 44.

After that, the image processing unit 44 performs a predetermined signal process on the first valid image signal (HDTV image signal) and the second valid image signal (SDTV image signal) which are output from the first valid data generation unit 435 and the second valid data generation unit 436, respectively, to generate an image signal including an in-vivo image. Therefore, the two image signals having different clock rates can be displayed by the display device 5.

According to the above-described embodiment, with respect to the two image signals having different clock rates, the transmission unit generates two valid signals based on the two image signals and synchronizes another valid signal with the valid signal generated based on the image signal having the highest clock rate, and generates the two valid image signals having different clock rates based on the valid signals, so that a plurality of image signals in different standards can be transmitted by a simple configuration.

In addition, in the embodiment, although the transmission of the two image signal having different clock rates is described, but the above-described transmission process may be applied to three or more image signals. For example, in the case where three image signals having different clock rates are generated by the image signal generation unit 42, among the valid signals generated based on the image signals, the valid signal of the image signal having the highest clock rate is set as the first valid signal, the valid signal of the image signal having the next highest clock rate is set as the second valid signal, and the valid signal of the remaining image signal is set to the third valid signal. After that, the second and the third valid signals are synchronized with each other so that the valid timing of the second valid signal and the valid timing of the third valid signal are included in the valid timing of the first valid signal, and the valid image signals are generated from the image signals based on the first to third valid signals. At this time, the timing signal generation unit generating the second valid signal and the third valid signal functions as the second timing signal generation unit, and the second valid signal and the third valid signal correspond to the second timing signals.

In addition, in the embodiment, although the signal processing unit 41, the image signal generation unit 42, and the transmission unit 43 are described to be installed inside the processing device 4, such processing blocks may be installed to the endoscope 2 (for example, a connector portion connected to the operating unit 22 or the processing device 4 of the universal cord 23).

In addition, in the embodiment, although the transmission unit 43 is described to receive a plurality of the image signals generated by the image signal generation unit 42 and process the plurality of the image signals, the transmission unit may receive the image signals (for example, a plurality of image signals generated by a plurality of imaging systems generating signals having different clock rates installed in the endoscope 2 side) in different standards received from the outside and process the plurality of the image signals.

In addition, in the above-described embodiment, the light source device 3 is described as a device separated from the processing device 4. However, the light source device 3 and the processing device 4 may be an integrated device, and for example, the light source 31 and the light source driver 32 are provided inside the processing device 4.

INDUSTRIAL APPLICABILITY

In this manner, the transmission system and the processing device according to the present disclosure are useful for transmitting a plurality of image signals in different standards by a simple configuration.

According to the present disclosure, it is possible to obtain an effect that a plurality of image signals in different standards can be transmitted by a simple configuration.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A processing device comprising:
a processor comprising hardware, wherein the processor is configured to:
  acquire an imaging signal representing an image captured inside an object;
  generate first and second image signals based on the imaging signal;
  receive the first image signal having the highest clock rate among the first and second image signals and generate a first timing signal representing valid timing and invalid timing of the first image signal;
  receive the second image signal having a resolution different from the first image signal and generate a second timing signal representing valid timing and invalid timing of the second image signal, each valid timing of the second timing signal being synchronized with the valid timing of the first timing signal;
  receive the first timing signal and the second image signal and output the second image signal based on the first timing signal,
  perform a transmission process comprising receiving the first and second timing signals and the first and second image signals and individually outputting the first timing signal and a process signal including the first and second image signals and the second timing signal,
  perform a first valid data generation comprising receiving the first timing signal from the transmission process, receiving only data according to valid timing of the first timing signal in the first image signal from the process signal to generate a first valid image signal, and receiving only data according to valid timing of the first timing signal in the second image signal and the second timing signal from the process signal to output the received second image signal and the received second timing signal; and
  receive the second timing signal from the first valid data generation and receive only data according to valid timing of the second timing signal in the second image signal to generate a second valid image signal; and
  apply a signal process for display image to the first and second valid image signals.

* * * * *